US012399161B2

(12) United States Patent
Iwata (10) Patent No.: US 12,399,161 B2
(45) Date of Patent: Aug. 26, 2025

(54) METHOD FOR ANALYZING COFFEE COMPONENT

(71) Applicant: Shimadzu Corporation, Kyoto (JP)

(72) Inventor: Natsuki Iwata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 311 days.

(21) Appl. No.: 18/115,442

(22) Filed: Feb. 28, 2023

(65) Prior Publication Data

US 2023/0288383 A1  Sep. 14, 2023

(30) Foreign Application Priority Data

Mar. 11, 2022 (JP) .................. 2022-038253

(51) Int. Cl.

| | | |
|---|---|---|
| *G01N 30/74* | (2006.01) | |
| *G01N 30/02* | (2006.01) | |
| *G01N 30/86* | (2006.01) | |
| *G01N 33/14* | (2006.01) | |

(52) U.S. Cl.
CPC ......... *G01N 30/74* (2013.01); *G01N 30/8631* (2013.01); *G01N 33/14* (2013.01); *G01N 2030/027* (2013.01)

(58) Field of Classification Search
CPC .... G01N 30/74; G01N 30/8631; G01N 33/14; G01N 2030/027
See application file for complete search history.

(56) References Cited

FOREIGN PATENT DOCUMENTS

| CN | 113336755 A | * | 9/2021 |
|---|---|---|---|
| JP | 6259146 B1 | | 1/2018 |

OTHER PUBLICATIONS

Atlabachew et al. Rapid and simultaneous determination of trigonelline, caffeine, and chlorogenic acid in green coffee bean extract. Food Sci Nutr. Jul. 5, 2021;9(9):5028-5035. doi: 10.1002/fsn3. 2456. PMID: 34532014; PMCID: PMC8441463. (Year: 2021).*
english translation of CN113336755 accessed from worldwide. espacenet.com.*
Arai et al., Simultaneous Determination of Trigonelline, Caffeine, Chlorogenic Acid and Their Related Compounds in Instant Coffee Samples by HPLC Using an Acidic Mobile Phase Containing Octanesulfonate, Aug. 2015, pp. 831-835, vol. 31, Analytical Sciences, The Japan Society for Analytical Chemistry.

(Continued)

*Primary Examiner* — Kristina M Deherrera
*Assistant Examiner* — Jean F Morello
(74) *Attorney, Agent, or Firm* — Paratus Law Group, PLLC (57) ABSTRACT

A method for analyzing coffee components includes, in this order, preparation step of preparing a sample solution containing coffee components extracted from coffee beans; dilution step of diluting the sample solution; and detection step of detecting the coffee components by performing liquid chromatography on the diluted sample solution. The detection step includes passing the sample solution through a column packed with a packing material having pentafluorophenylpropyl group, and then detecting trigonelline and pyrocatechol in the passed sample solution by a photodiode array ultraviolet-visible absorbance detector.

4 Claims, 6 Drawing Sheets

(56) References Cited

OTHER PUBLICATIONS

Iwata, Simultaneous quantitative analysis of functional ingredients in coffee, Shimadzu Corporation Application News, Jan. 2022, pp. 1-5.

Iwata, Monitoring of functional ingredient content by roasting time of coffee, Shimadzu Corporation Application News, Feb. 2022, pp. 1-5.

Asano, Studies on the Octopus Extract (II)—Quaternary Ammonium Bases and Nucleic Acid Relating Compounds, Yokohama National University Bulletin of Education, Oct. 30, 1984, pp. 199-207, vol. 24.

* cited by examiner

METHOD FOR ANALYZING COFFEE COMPONENT

BACKGROUND OF THE INVENTION

Cross Reference to Related Applications

This application claims priority to Japanese Patent Application No. 2022-038253 filed on Mar. 11, 2022, the entire disclosure of which is incorporated by reference herein.

Field of the Invention

The present invention relates to a method for analyzing coffee components.

Description of the Related Art

Functional components of foodstuffs have been heretofore studies. Among them, coffee components extracted from coffee beans have also been studied, and in recent years, trigonelline and pyrocatechol that are coffee components have been reported to be linked to a preventive effect or an ameliorating effect on lifestyle-related diseases such as dementia, diabetes and cancer. Similarly, chlorogenic acid has also been reported to exhibit an antioxidant action and have an inhibitory effect on aging.

As a method for analyzing functional components such as the above-mentioned coffee components, liquid chromatography is generally employed. For example, JP-B-6259146, chlorogenic acid which is highly hydrophobic is separated by reversed phase chromatography, and trigonelline which is a hydrophilic compound is not retained by reversed phase chromatography, and therefore is retained by hydrophilic interaction chromatography which is a type of normal phase chromatography. In Kana ARAI et al. ANALYTICAL SCIENCES, August 2015, Volume 3, p. 831-835, both trigonelline and chlorogenic acid are simultaneously separated by reversed phase chromatography using an ion pair reagent.

However, the method according to JP-B-6259146 requires time and labor because it is necessary to separately perform two types of liquid chromatography. In particular, hydrophilic interaction chromatography is poorly stable analysis, i.e. retention time reproducibility, and requires securement of a sufficient time for column equilibration for improvement of the analysis stability. In the method according to Kana ARAI et al. ANALYTICAL SCIENCES, August 2015, Volume 3, p. 831-835, an ion pair reagent is used, so that a conditioning time for modifying a stationary phase with the ion pair reagent is required. It takes a long time before the start of analysis with the conditioning time being generally about 2 to 3 hours. Because of poor compatibility with a gradient elution method in which the ratio of solvents in a mobile phase is changed during analysis to complete the analysis in a short time, the analysis is performed by an isocratic elution method in which the ratio of solvents in a mobile phase is fixed, and therefore it takes a long time for the analysis itself.

The two documents neither disclose analysis of pyrocatechol being important, nor indicate that both trigonelline and pyrocatechol which are effective against lifestyle-related diseases are simultaneously analyzed.

SUMMARY OF THE INVENTION

Accordingly, an object of the present invention is to provide a method by which trigonelline and pyrocatechol that are coffee components can be conveniently analyzed in a short time.

An analytical method according to a first aspect of the present invention is a method for analyzing a coffee component, the method including, in this order: preparation step of preparing a sample solution containing the coffee component extracted from coffee beans; dilution step of diluting the sample solution; and detection step of detecting the coffee component by performing liquid chromatography on the diluted sample solution, the detection step including passing the sample solution through a column packed with a packing material having pentafluorophenylpropyl groups, and then detecting trigonelline and pyrocatechol in the passed sample solution by a photodiode array ultraviolet-visible absorbance detector.

By the analytical method according to the first aspect, trigonelline and pyrocatechol that are coffee components can be conveniently analyzed in a short time.

DETAILED DESCRIPTION OF THE PREFERRED EMBODIMENTS

1. First Embodiment

The analytical method according to the first embodiment of the present invention includes preparation step, dilution step, and detection step in this order. Hereinafter, each step will be described in detail.

(Preparation Step)

In the present step, a sample solution containing coffee components is prepared.

The coffee components are the components extracted from coffee beans. The coffee components are eluted from the coffee beans by roasting and grinding the coffee beans at a high temperature (e.g. 150° C. to 250° C.) and bringing the resulting ground product into contact with water or hot water. Specific examples of the coffee components include trigonelline, pyrocatechol, chlorogenic acid, caffeine, and caffeic acid. In addition thereto, contaminants in coffee beans are contained in the sample solution.

In the first embodiment, both trigonelline and pyrocatechol that are expected to have a preventing or ameliorating effect on lifestyle-related diseases are simultaneously analyzed as coffee components. Preferably, the chlorogenic acid expected to have an anti-aging effect is also simultaneously analyzed. That is, the three components of trigonelline, pyrocatechol and chlorogenic acid are analyzed simultaneously. More preferably, the five components of trigonelline, pyrocatechol, chlorogenic acid, caffeine and caffeic acid that are major coffee components are analyzed simultaneously.

(Dilution Step)

In this step, the sample solution obtained in the preparation step is diluted. In this way, a diluted sample solution (dilute sample solution) is prepared.

Examples of the solvent for dilution include water and organic solvents, and water is preferable.

The dilute concentration may be appropriately determined according to the concentration of coffee components that are extracted. When coffee obtained by general extraction is analyzed, the coffee may be diluted by a factor of, for example, 2 or more, preferably 5 or more and, for example, 100 or less, preferably 50 or less. This enables coffee components to be detected with high sensitivity while contamination of a device such as a column is suppressed.

(Detection Step)

In the present step, liquid chromatography is performed on the diluted sample solution. In this way, coffee components are separated and detected.

In liquid chromatography, the sample solution is mixed with an eluent (mobile phase), and the mixture is passed through a column to separate components in the sample solution from one time to another. As an apparatus used for liquid chromatography, a known liquid chromatographic apparatus or analyzer may be used, and for example, Nexera Series manufactured by Shimadzu Corporation is commercially available.

Examples of the eluent include organic solvents and water. Examples of the organic solvent include acetonitrile, methanol, ethanol, 2-propanol, acetone, chloroform, and tetrahydrofuran. These organic solvents can be used alone or in combination of two or more thereof. Acetonitrile is preferable. This enables coffee components to be reliably detected.

In the first embodiment, a gradient elution method is preferably employed. That is, the concentration of the organic solvent in the mobile phase is gradually increased from the beginning of the analysis. For adjustment of the concentration of the organic solvent, a buffer solution such as a phosphate buffer solution may be used. This enables the analysis completion time to be shortened while the peak separation in each component is improved.

The column mounted in the liquid chromatograph is packed with packing material having pentafluorophenylpropyl group. That is, the sample solution is passed through a column packed with a packing material having pentafluorophenylpropyl group (pentafluorophenyl group). Such packing material is obtained by chemically bonding pentafluorophenylpropyl group to silica gel. Specific examples thereof include Shim-Pack Scepter PFPP (registered trademark) manufactured by Shimadzu Corporation, and Inert-Sustain PFP manufactured by GL Sciences Inc. In the first embodiment, stationary phase in the column has pentafluorophenylpropyl group, the pentafluorophenylpropyl group has higher hydrophobicity as compared to a mixed solution of an acidic buffer and an organic solvent which is used as a mobile phase, and the separation behavior of reversed phase chromatography is exhibited. Caffeine undergoes $\pi$-$\pi$ interaction and CH/$\pi$ interaction in addition to hydrophobic interaction, and is retained to a larger extent than the C18 stationary phase. Pyrocatechol, chlorogenic acid and caffeic acid have higher hydrophobicity over the mobile phase, and the pentafluorophenylpropyl group also has high hydrophobicity, so that between the former and the latter, interaction caused by affinity between hydrophobic pairs is applied. Pyrocatechol is less hydrophobic than chlorogenic acid and caffeic acid having a catechol skeleton, and is retained to a lesser extent than any other of these three components. On the other hand, for trigonelline having high hydrophilicity, it is thought that since the pentafluorophenylpropyl group is polarized to a large extent, and trigonelline is also polarized as it is an electron donating compound having a positively charged pyridine cyclic structure, interaction caused by a Coulomb force between polar molecules is applied. The first embodiment is not limited to the above-described mechanism.

The column temperature is, for example, 50° C. or lower, preferably 30° C. or lower, more preferably 28° C. or lower, and for example, 5° C. or higher, preferably 10° C. or higher. When the column temperature is the above-described upper limit or lower, peak separation is improved. When the column temperature is 3000 or lower, separation between the peak of a foreign substance and the peak of trigonelline is clarified, so that quantitative analysis of trigonelline can be more accurately performed.

As a detector, a photodiode array (semiconductor element) ultraviolet-visible absorbance detector (hereinafter, abbreviated as a "photodiode array detector") is used. That is, the sample solution passed through the column (in other words, a separation solution having coffee components separated from the sample solution from one time to another) is detected by the photodiode array detector. Specifically, a sample solution in a flow cell is irradiated with predetermined light (e.g. a mixture of tungsten lamp light and D2 lamp light), the light transmitted therethrough is dispersed by a diffraction grating, and light at each wavelength is detected by the photodiode array detector. A graph showing the intensity of light (particularly the absorbance of the separation solution) on the basis of the retention time is output as a chromatogram by analyzing the detected light or processing the data. This chromatogram is obtained for each of a plurality of wavelengths arbitrarily set in the photodiode array detector. Since a UV spectrum (such as an absorption spectrum) for the separation solution at a specific retention time can be obtained, a UV spectrum can be obtained for each of the separated coffee components. That is, by using the photodiode array detector, a chromatogram for each of a plurality of wavelengths can be obtained, and a UV spectrum for each of coffee components separated can also be obtained.

Preferably, the detection is performed at a plurality of wavelengths. Examples thereof include a wavelength of 260 nm or more and 280 nm or less (hereinafter, referred to as a first wavelength), and a wavelength of 315 nm or more and 335 nm or less (hereinafter, referred to as a second wavelength). In particular, at the first wavelength, all of trigonelline, pyrocatechol, chlorogenic acid, caffeine and caffeic acid absorb light having the first wavelength, so that spectroscopic analysis is possible. At the second wavelength, in particular, chlorogenic acid and caffeic acid strongly absorb light having the second wavelength, so that the accuracy of detection of these two components can be improved.

In the chromatogram obtained by this step, in particular, the chromatogram detected at the first wavelength, peaks corresponding to trigonelline, pyrocatechol, chlorogenic acid, caffeine and caffeic acid are observed in different retention time ranges. In particular, peaks of the five components are observed over a retention time of 3 minutes or more and 15 minutes or less.

This enables coffee components in the sample solution to be analyzed simultaneously. Specifically, trigonelline and pyrocatechol can be analyzed simultaneously. Preferably, the three components of trigonelline, pyrocatechol and chlorogenic acid can be analyzed simultaneously. Most preferably, the five components of trigonelline, pyrocatechol, chlorogenic acid, caffeine and caffeic acid can be analyzed simultaneously.

In the first embodiment, preparation of a calibration curve enables quantitative analysis of the coffee components. Specifically, for each coffee component, a plurality of standard solutions having a known concentration are prepared, and the detection step is carried out to obtain chromatograms corresponding to a plurality of concentrations, thereby preparing a calibration curve (a graph obtained by plotting a relationship between the peak intensity and the known concentration) for each component. The peak intensity of coffee components in a sample solution having an unknown concentration can be associated with the calibration curve to determine the concentration of the coffee components. In the first embodiment, the concentration of the coffee components can be measured with excellent accuracy because the calibration curve graph has very good linearity.

In the first embodiment, the coffee components can be identified by outputting an absorption spectrum such as a UV spectrum. Specifically, a UV spectrum is acquired for a specific peak in the chromatogram, and the UV spectrum is compared with a UV spectrum for a known coffee component. This enables reliable determination of whether the specific peak in the chromatogram is a peak from an intended coffee component. This enables an intended coffee component to be accurately identified and is therefore effective in the case where the sample solution contains various foreign substances and peaks of various foreign substances are detected in the chromatogram.

By the analytical method according to the first embodiment, coffee components can be analyzed, and in particular, trigonelline, pyrocatechol, chlorogenic acid, caffeine and caffeic acid can be separated, detected and quantified from the sample solution simultaneously. The analytical method is convenient because coffee components can be analyzed simultaneously in one liquid chromatography using one column. Analysis can be performed in a short time because it is not necessary to use an ion pair reagent or the like and a lot of conditioning time is not required. The column can be reused because degeneration of the stationary phase by the ion-pair reagent does not occur. Good analysis accuracy is obtained because the chromatogram obtained has good reproducibility of the retention time and the peak area. The concentration of the coffee components can be accurately measured because a calibration curve having high linearity and little variation can be prepared. The coffee components can be more accurately discriminated and quantified because a peak of a foreign substance and the peaks of the coffee components can be detected separately, and identification by a UV spectrum is possible.

2. Aspects

Those skilled in the art understand that the exemplary embodiments described above are specific examples of the following aspects.

(Item 1) A method for analyzing coffee components according to an aspect may include, in this order: preparation step of preparing a sample solution containing coffee components extracted from coffee beans; dilution step of diluting the sample solution; and detection step of detecting the coffee components by performing liquid chromatography on the diluted sample solution, the detection step including passing the sample solution through a column packed with a packing material having pentafluorophenylpropyl group, and then detecting trigonelline and pyrocatechol in the passed sample solution by a photodiode array ultraviolet-visible absorbance detector.

(Item 2) In the analytical method according to Item 1, a wavelength of light for detecting the coffee components by the photodiode array ultraviolet-visible absorbance detector may be at least a wavelength of 260 nm or more and 280 nm or less and a wavelength of 315 nm or more and 335 nm or less.

(Item 3) In the analytical method according to Item 1 or 2, a temperature of the column may be 30° C. or lower.

(Item 4) In the analytical method according to any one of Items 1 to 3, in the detection step, trigonelline, pyrocatechol, chlorogenic acid, caffeine and caffeic acid may be detected simultaneously.

EXAMPLES

The present invention will now be described in detail by giving examples, which should not be construed as limiting the scope of the present invention.

Example 1

(Analysis of Mixed Standard Solution)

Figure 1:
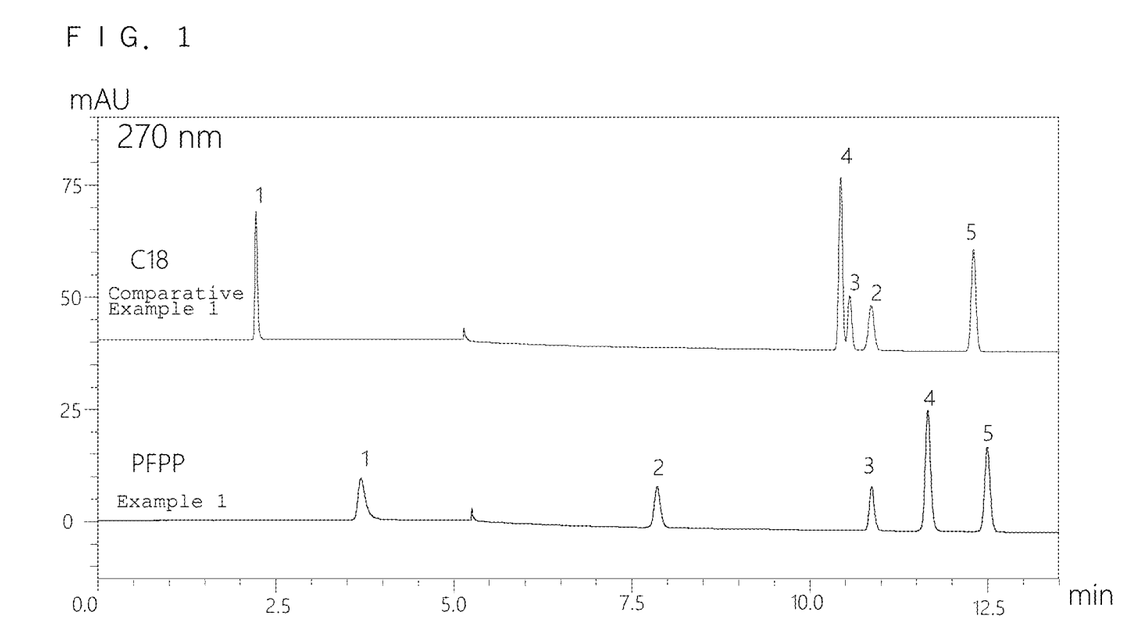
FIG. 1 shows chromatograms of Example 1 and Comparative Example 1 in which a mixed standard solution is analyzed under the condition of a wavelength of 270 nm, where the vertical axis represents a peak intensity, the horizontal axis represents a retention time, the upper part of the chromatogram shows the result of Comparative Example 1 (using a C18 stationary phase), and the lower part of the chromatogram shows the result of Example 1 (using a PFPP stationary phase)
Figure 2:
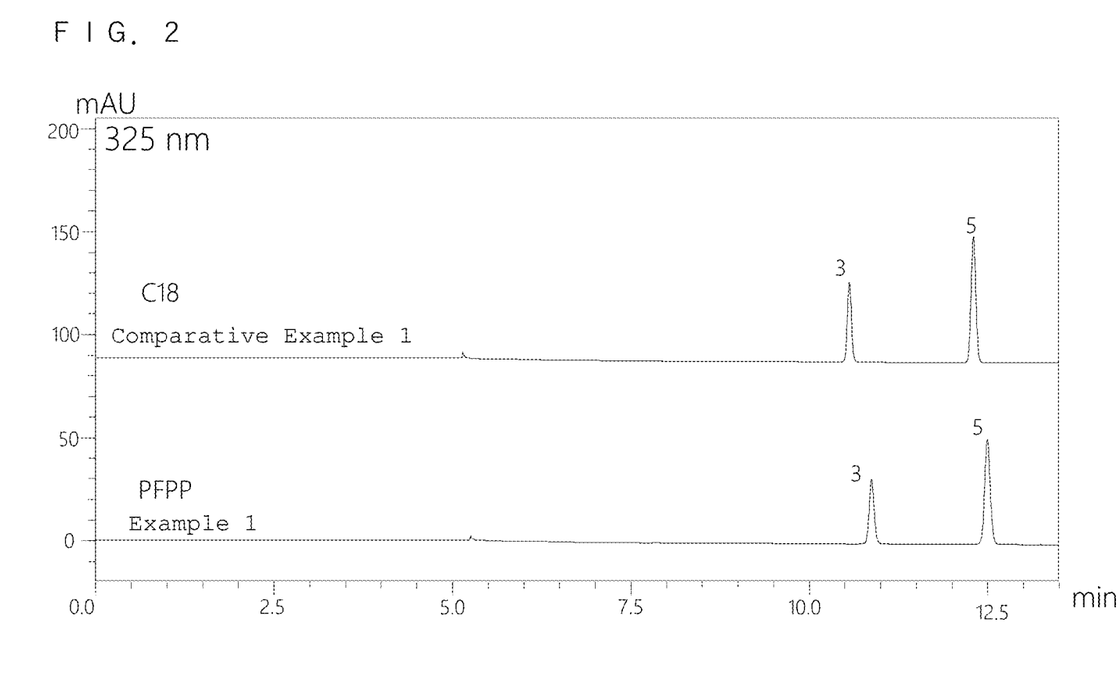
FIG. 2 shows chromatograms in which a mixed standard solution is analyzed under the condition of a wavelength of 325 nm.

A mixed standard solution containing 10 mg/L of each of trigonelline, pyrocatechol, chlorogenic acid, caffeine and caffeic acid was prepared, and liquid chromatography was performed under the following conditions. The column was packed with packing material having pentafluorophenylpropyl group (PFPP), and a photodiode array detector was used as a detector. For the results, chromatograms at a detection wavelength of 270 nm are shown in FIG. 1, and chromatograms at a detection wavelength of 325 nm are shown in FIG. 2.

Apparatus name: Nexera lite (Ultra High Performance Liquid Chromatograph manufactured by Shimadzu Corporation)
Column: Shim-pack Scepter PFPP-120 (150 mm×4.6 mm I.D., 3 μm)
Flow rate: 1.0 mL/min
Mobile phase: A) 20 mmol/L (Sodium) phosphate buffer (pH 2.6)
B) Acetonitrile
Gradient elution method, 0% B (0.00-1.00 min), 10% B (4.00 min), 20% B (10.00-12.00 min), 70% B (12.01-13.00 min), 0% B (13.01-18.00 min)
Mixer: 180 μL
Column temperature: 25° C.
Injection amount: 5 μL
Detector: Photodiode array (PDA) ultraviolet-visible absorbance detector ("SPD-M40" manufactured by Shimadzu Corporation)
Detection wavelength: 270 nm, 325 nm In FIGS. 1 and 2, since five peaks were observed, it was possible to separate and detect five components (trigonelline, pyrocatechol, chlorogenic acid, caffeine and caffeic acid) as coffee components. The five components were shown to have been appropriately retained and separated in the column because all the peaks satisfied 3 minutes or more, which is an optimum retention time recommended based on flowrate of mobile phase and column size. The analysis was shown to have been completed in a short time because the retention time for the five components was 13.5 minutes or less.

Individual standard solutions each containing only one coffee component were also prepared, the liquid chromatography was performed, and each component was associated with its peak to confirm that the peak "1" was derived from trigonelline, the peak "2" was derived from pyrocatechol, the peak "3" was derived from chlorogenic acid, the peak "4" was derived from caffeine, and the peak "5" was derived from caffeic acid.

Comparative Example 1

The same procedure as in Example 1 was performed except that the column was changed to a column packed with a C18 stationary phase (Shim-pack Scepter C18-120 (150 mm×4.6 mm I.D., 3 μm)). For the results, chromatograms at a detection wavelength of 270 nm are shown in FIG. 1, and chromatograms at a detection wavelength of 325 nm are shown in FIG. 2.

In Comparative Example 1, the peak "1", i.e. a peak indicating trigonelline was detected at a retention time of 2.1 minutes, position where the retention time was 2.1 minutes, and this was not suitable because the retention time did not satisfy an optimum retention time of 3 minutes or more.

(Reproducibility of Retention Time)

A mixed standard solution containing 1 mg/L of each of the five components was prepared, and the same analysis as described above was repeated six times. Here, the relative standard deviations (RSDs) of the retention time and the peak area for each peak were calculated. Table 1 below shows the results.

TABLE 1

| Compound | Standard deviation of retention time (%) | Standard deviation of peak area (%) |
| --- | --- | --- |
| Trigonelline | 0.08 | 0.65 |
| Pyrocatechol | 0.05 | 0.50 |
| Chlorogenic acid | 0.07 | 0.14 |
| Caffeine | 0.06 | 0.15 |
| Caffeic acid | 0.05 | 0.21 |

Regarding the retention time, the standard deviation was less than 0.1% for all the five components. Regarding the peak area, the standard deviation was less than 0.7% for all the five components. These results showed very low variation and excellent reproducibility for both the retention time and the peak area.

(Preparation of Calibration Curve)

For each of the five components, individual standard solutions having different concentrations were prepared, and the same analysis as described above was performed to prepare a calibration curve. Table 2 below shows calibration curve concentration ranges and contribution ratios in these calibration curves. The calibration curves for trigonelline and pyrocatechol are shown in FIG. 3.

TABLE 2

| Compound | Concentration range (mg/L) | Contribution ratio $\gamma^2$ |
| --- | --- | --- |
| Trigonelline | 1-100 | 0.99999 |
| Pyrocatechol | 0.1-10 | 0.99999 |
| Chlorogenic acid | 1-100 | 0.99999 |
| Caffeine | 1-100 | 0.99999 |
| Caffeic acid | 0.1-10 | 0.99999 |

Figure 3:
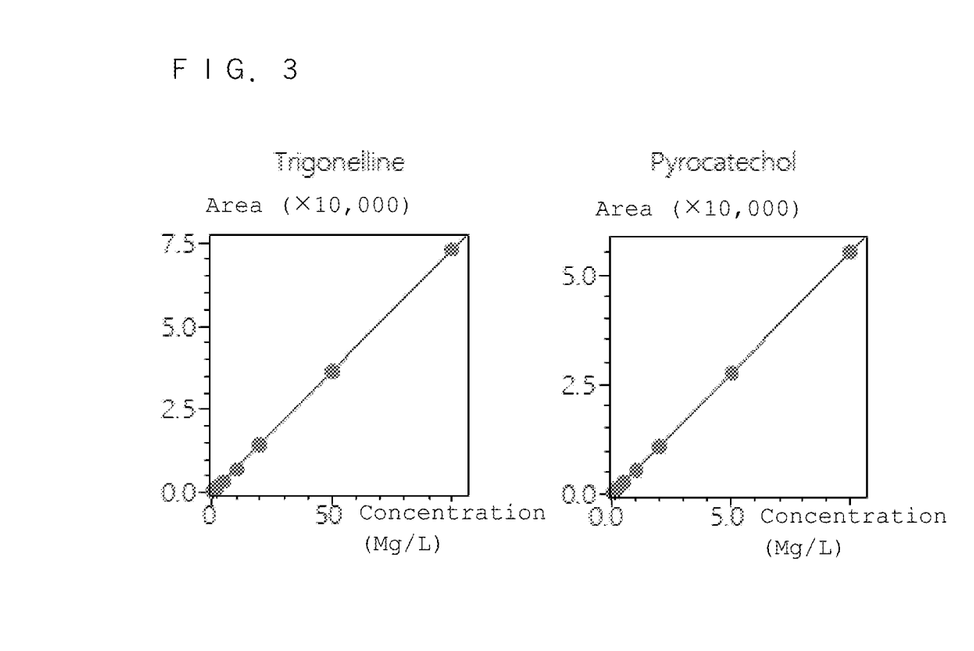
FIG. 3 shows calibration curves for trigonelline and pyrocatechol.

Excellent linearity was obtained with the contribution ratio being 0.9999% or more for all the five components in Table 2 and FIG. 3, and therefore these calibration curves were shown to be effectively used.

Example 2

(Analysis of Coffee)

Figure 4:
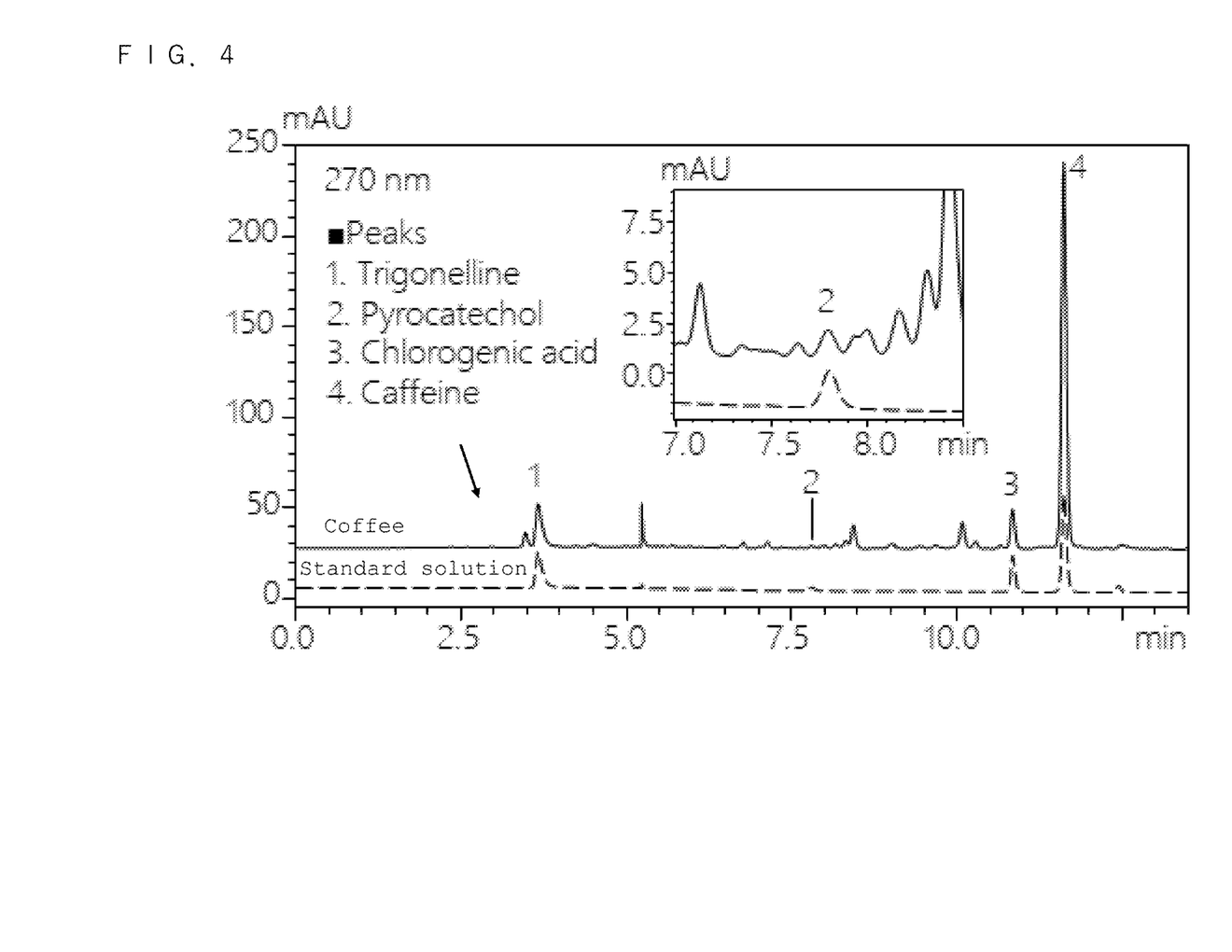
FIG. 4 shows chromatograms of Example 2 in which coffee and a mixed standard solution are analyzed under the condition of a wavelength of 270 nm, where the vertical axis represents a peak intensity, the horizontal axis represents a retention time, the upper part of the chromatogram shows the result for the coffee, and the lower part of the chromatogram shows the result for the standard solution.
Figure 5:
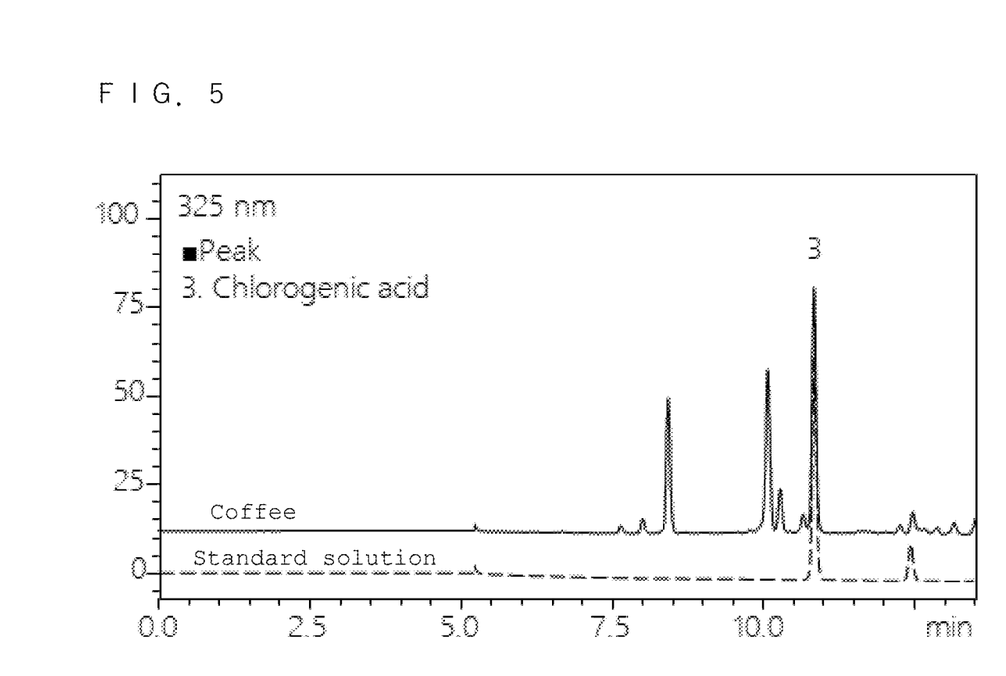
FIG. 5 shows chromatograms of Example 2 in which coffee and a mixed standard solution are analyzed under the condition of a wavelength of 325 nm.
Figure 6:
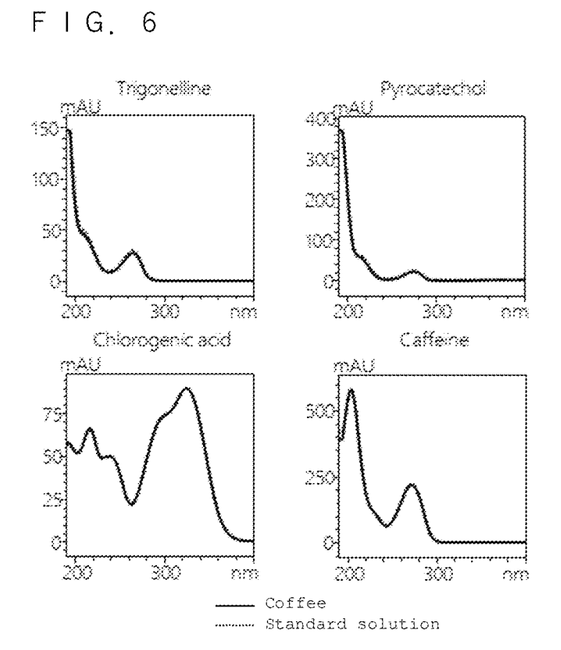
FIG. 6 shows UV spectra of separation solutions and individual standard solutions at the peaks of coffee, where the solid line shows the result for the coffee and the broken line shows the result for the individual standard solution.

An extract obtained by extracting 10 g of commercially available ground coffee beans with 150 mL of hot water was filtered with a 0.2 μm membrane filter. Thereafter, the filtrate was diluted ten-fold with ultrapure water to prepare a sample solution. Using this sample solution, liquid chromatography was performed under the same analysis conditions as in Example 1. For this result, a chromatogram (solid line) at a detection wavelength of 270 nm is shown in FIG. 4, and a chromatogram (solid line) at a detection wavelength of 325 nm is shown in FIG. 5. For the peaks "1" to "4", UV spectra at 200 nm to 400 nm were measured. The results are shown in FIG. 6. The concentrations of the components were determined on the basis of the calibration curves described above. The analysis of the sample solution and the determination of the concentration of the sample solution were repeated six times, and a relative standard deviation was calculated. Table 3 below shows the results.

TABLE 3

| Compound | Concentration (mg/L) | Relative standard deviation (%) |
| --- | --- | --- |
| Trigonelline | 21.5 | 0.08 |
| Pyrocatechol | 1.0 | 1.05 |
| Chlorogenic acid | 21.3 | 0.07 |
| Caffeine | 79.2 | 0.05 |
| Caffeic acid | Not detected | Not detected |

(Analysis of Standard Solution)

A mixed standard solution containing trigonelline at 20 mg/L, pyrocatechol at 2 mg/L, chlorogenic acid at 20 mg/L, caffeine at 20 mg/L and caffeic acid at 2 mg/L was prepared, and liquid chromatography was performed under the same analysis conditions as in Example 1. A chromatogram (broken line) with this mixed standard solution is shown in FIGS. 4 and 5. UV spectra at 200 nm to 400 nm were measured for individual standard solutions of trigonelline, pyrocatechol, chlorogenic acid and caffeine. The results are shown in FIG. 6.

(Discussion)

As in FIGS. 4 and 5, peaks "1" to "4" were also observed in the chromatograms for the coffee components extracted from the coffee beans. As in FIG. 6, the spectra of the individual standard solutions completely matched the UV spectra of the peaks "1" to "4". These results showed that the peaks of "1" to "4" corresponded to trigonelline, pyrocatechol, chlorogenic acid and caffeine, respectively, and these components were contained in the coffee. Since a peak corresponding to caffeic acid was not observed, it can be determined that caffeic acid is not contained in the coffee. The analytical method was also excellent in quantitativeness with a small standard deviation. In FIG. 4, a small peak (see an arrow) is detected before the peak "1", and this is derived from a foreign substance, showing that in the analytical method of the present invention a foreign substance was separated.

Example 3

Coffee different in roasting time was prepared, and the liquid chromatography was performed in the same manner as in Example 1. Here, the analyses were performed at different column temperatures of 25° C., 30° C. and 35° C., respectively. These results showed that at 25° C., the peak of trigonelline was completely separated from the peak of a foreign substance immediately therebefore. At 30° C., the trigonelline peak was close to the peak of the foreign substance, and the tails of both peaks very slightly overlapped each other. At 35° C., those peaks overlapped each other.

What is claimed is:

1. A method for analyzing coffee components, the method comprising, in this order:

preparation step of preparing a sample solution containing coffee components extracted from coffee beans;

dilution step of diluting the sample solution; and detection step of detecting the coffee components by performing liquid chromatography on the diluted sample solution, the detection step including passing the sample solution through a column packed with a packing material having pentafluorophenylpropyl group, and then detecting trigonelline and pyrocatechol in the passed sample solution by a photodiode array ultraviolet-visible absorbance detector.

2. The analytical method according to claim 1, wherein (1) a wavelength of 260 nm or more and 280 nm or less and (2) a wavelength 315 nm or more and 335 nm or less are used as wavelengths of light for detecting the coffee components by the photodiode array ultraviolet-visible absorbance detector.

3. The analytical method according to claim 1, wherein a temperature of the column is 30° C. or lower.

4. The analytical method according to claim 1, wherein in the detection step, trigonelline, pyrocatechol, chlorogenic acid, caffeine and caffeic acid are detected simultaneously.

* * * * *